US005777231A

United States Patent [19]
Patel et al.

[11] Patent Number: 5,777,231
[45] Date of Patent: Jul. 7, 1998

[54] ULTRASONIC SENSOR FOR ON-LINE DETECTION OF CUTTING TOOL INSERT FAILURE

[76] Inventors: Narendra D. Patel, 3 Benemar Ct., Hamilton, Ontario, Canada, L8W 2R1; Mohamed A. Elbestawi, 1394 Saddler Circle, Oakville, Ontario, Canada, L6M 2X5

[21] Appl. No.: 735,648

[22] Filed: Oct. 24, 1996

[51] Int. Cl.$^6$ ............................................. G01N 29/22
[52] U.S. Cl. ........................... 73/660; 73/629; 73/862.06
[58] Field of Search ............................... 73/597, 599, 629, 73/660, 104, 862.06; 364/474.17; 340/679, 680, 683

[56] References Cited

U.S. PATENT DOCUMENTS

4,927,300  5/1990  Ramalingam .................... 73/862.06
5,461,923  10/1995  Meisterling ........................... 73/597

Primary Examiner—Christine K. Oda
Attorney, Agent, or Firm—Lynn C. Schumacher; Dowell & Dowell, P.C.

[57] ABSTRACT

An on-line ultrasonic sensor for monitoring and sensing failure in a cutting tool insert. The preferred embodiment of the sensor includes a piezoelectric film of aluminum nitride (AlN) deposited onto a tool insert or tool insert seat with the AlN film electrically connected to a signal generator and detection circuitry. A voltage pulse is applied to the AlN film to generate ultrasonic signal pulses in the AlN film which are transmitted through a tool insert to the vicinity of the cutting edge of the tool insert during use. Back-reflected ultrasonic signals from the edge of the tool insert induce a voltage signal in the piezoelectric film which is analysed and compared to signals characteristic of undamaged tool inserts. Temperature increases, wear and various types of tool failure can be readily detected during use of the insert with the sensor.

21 Claims, 7 Drawing Sheets

ULTRASONIC SENSOR FOR ON-LINE DETECTION OF CUTTING TOOL INSERT FAILURE

FIELD OF THE INVENTION

The present invention relates to on-line ultrasonic sensors for detecting damage in tool inserts during use.

BACKGROUND OF THE INVENTION

The ability to monitor tool inserts during use for detection of wear, faults, temperature change, breakage, stress and cutting contact area is very important for automated manufacturing. The usefulness and reliability of the detection characteristics are directly dependent on the sensor placement relative to the cutting process. Placement of the sensor very near the cutting surface of either the tool insert or workpiece is desirable to provide measurements with minimal noise and signal distortion and with enhanced sensitivity. Known sensors currently in use for on-line monitoring of cutting tool inserts include accelerometers, microphones, AE sensors and force sensors. These sensors monitor wear, chipping and tool insert breakage and are based on pattern recognition which renders them slow and difficult to incorporate into automated systems.

It would be advantageous to provide an on-line detection method which allows direct monitoring of wear, temperature increase, chipping and breakage of tool inserts which can be readily incorporated into automated systems.

SUMMARY OF THE INVENTION

The present invention provides a method for detecting damage to a tool insert held in an insert holder and contacted with a workpiece in use. The method comprises producing ultrasonic signal pulses in a piezoelectric coating contacting a tool insert having a cutting edge with the ultrasonic signal pulses being directed through the tool insert substantially toward a surface region of the tool insert in close proximity to the cutting edge of the tool insert. The method includes detecting ultrasonic signal pulses responsively reflected from the surface region of the tool insert back through the tool insert into the piezoelectric coating and comparing the reflected ultrasonic signal pulses to a reference signal pulse reflected from the surface region before the tool insert is initially contacted to a workpiece.

In this aspect of the invention the piezoelectric coating is a film of aluminum nitride (AlN) having substantially <002> crystal orientation.

In another aspect of the invention there is provided an on-line ultrasonic sensor for monitoring a tool insert, the tool insert having a surface portion for contacting a workpiece and being mountable in an insert holder. The sensor comprises a piezoelectric coating in contact with a portion of the tool insert spaced from the surface portion. The sensor includes means for generating ultrasonic signal pulses in the piezoelectric coating with the ultrasonic signal pulses being directed through the tool insert substantially toward a surface region of the tool insert in close proximity to and including the surface portion. The sensor includes means for detecting and analysing ultrasonic signal pulses responsively reflected from the surface region of the tool insert back through the tool insert into the piezoelectric coating.

BRIEF DESCRIPTION OF THE DRAWINGS

An on-line ultrasonic sensor constructed in accordance with the present invention will now be described, by way of example only, reference being had to the accompanying drawings, in which.

DETAILED DESCRIPTION OF THE INVENTION

The on-line sensor of the present invention detects macroscopic and microscopic structural changes in cutting tool inserts by detecting changes in an ultrasonic signal. The sensor uses a high frequency ultrasound signal generated by a piezoelectric material directed to the cutting edge or tip of a tool insert where it is back-reflected. The back-reflected ultrasound signal is detected, analysed and compared to a back reflected signal (BARS) characteristic of undamaged cutting tool insert tips. It will be understood that the term insert, or tool insert, can include various types of devices which contact a work piece during machining operations. For example, when using a lathe to shape a workpiece, the cutting tool insert is clamped on a tool insert seat in a holder and the cutting tool insert cuts into the workpiece during lathing. However the method and device disclosed herein will be generally applicable to other types of tool inserts which contact the workpiece during use, such as grinding inserts and the like.

I) Sensor Construction

Figure 1:
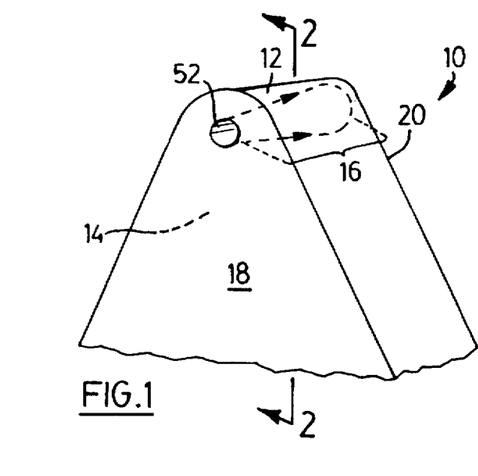
FIG. 1 is a perspective view of a cutting tool insert with an ultrasonic sensor mounted thereon in accordance with the present invention.
Figures 2, 3B:
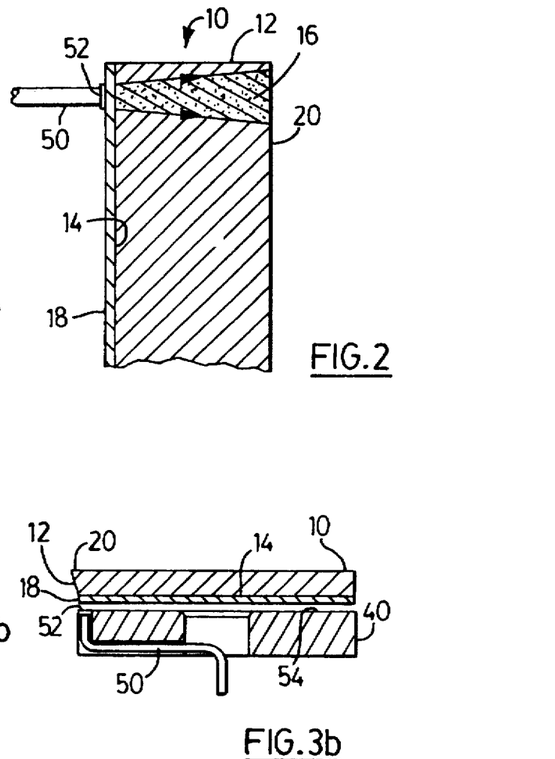
FIG. 2 is a cross sectional view along the line 2—2 in FIG. 1.
FIG. 3(b) is a sectional view along the line 3(b)—3(b) of FIG. 3(a) with the cutting tool of FIG. 1 shown in cross section adjacent to the insert seat.
Figure 3A:
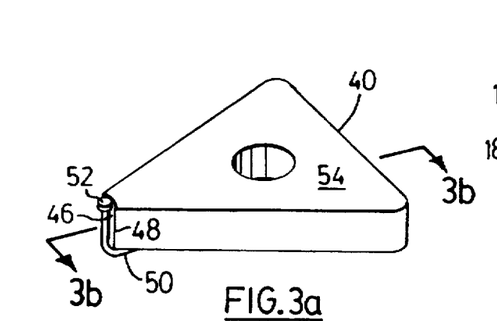
FIG. 3(a) is a perspective view of a carbide insert seat modified in accordance with the present invention.
Figure 3C:
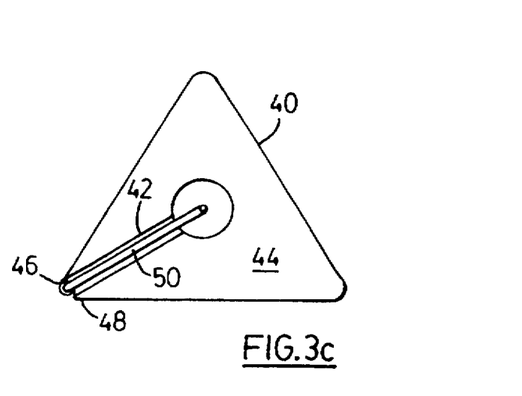
FIG. 3(c) is a bottom view of the insert seat of FIG. 3(a)
Figure 3D:
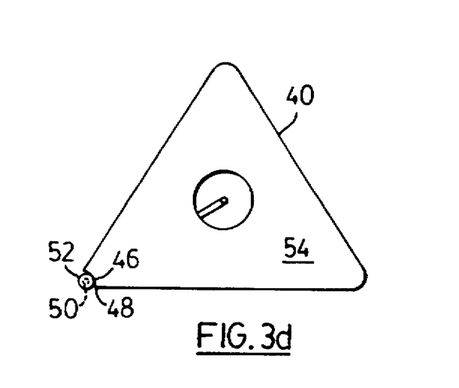
FIG. 3(d) is a top view of the insert seat of FIG. 3(a)

The general principle of the present invention is shown in FIGS. 1 and 2. A cutting tool insert 10 includes a cutting edge 12 and a bottom surface 14. A film or coating of a piezoelectric material 18, preferably aluminum nitride (AlN), is coated onto the bottom surface 14 of the insert 10 and extends out to the cutting edge 12. A flat, planar end 52 of a wire 50 abuts against film 18 in use, and provides a means for generating an ultrasonic signal in insert 10. A beam of high frequency ultrasound 16 is shown directed toward and impinging on a top surface 20 of the insert close to the cutting edge 12. The beam 16 is represented in FIG. 1 as a shaded area extending through the solid cutting tool insert 10.

This particular embodiment and associated insert holder is illustrated in more detail in FIGS. 3(a) to 3(d). Referring to FIGS. 4(a) to 4(e), another embodiment of the on-line sensor in accordance with the invention involves depositing a piezoelectric film 18' onto the surface 68 of seat 60 which is located adjacent to the bottom face of the cutting tool insert when the insert and seat are assembled with the insert holder. These different embodiments of the structure of the on-line sensor will be discussed below first followed by a description of the preferred method of growth of the AlN film.

Referring to FIGS. 3(a) to 3(d), an electrically conductive carbide seat 40 is shown modified to support the cutting tool insert 10 with the bottom face 14 having a piezoelectric layer 18 deposited thereon, shown only in FIG. 3(b). The carbide insert seat 40 is provided with a groove 42 along the bottom surface 44 and a groove 46 along the thickness of an apex 48 of the seat. Grooves 42 and 46 are preferably of a diameter suitable to receive therein a 0.5 to 2.0 mm diameter insulated wire 50 which is bonded to the carbide seat 40 with a high temperature epoxy. The exposed end face 52 of wire 50 is flush with the top surface 54 of the carbide seat 40 so that when the cutting tool insert 10 is clamped to the seat, the electrically insulating AlN layer 18 adhered to the bottom surface 14 contacts the exposed end portion 52 of the wire. The other end of wire 50 is coupled to a signal generating and processing means (not shown) described hereinafter. Wire 50 is electrically insulated from carbide seat 40 by the insulation surrounding the wire. When carbide seat 40 is clamped into a grounded metallic cutting tool insert holder (not shown) it is electrically grounded through the holder and the exposed end portion 52 of wire 50 does not electrically contact the carbide seat.

If a material other than carbide is used as the insert seat which is an electrical insulator, then a metal layer such as platinum is preferably deposited onto top surface 54 of the seat in order to provide an electrical contact for grounding the seat through the metal insert holder. This is done prior to deposition of the AlN film on the insert material for the material described above. With the second technique (described below) in which the wires are embedded in a ceramic seat, the metal layer is deposited onto surface 54 of the seat.

A preferred embodiment of the on-line ultrasonic sensor of the present invention is shown in FIGS. 4(a) to 4(e) which is formed by depositing a piezoelectric film directly onto the surface of the seat which normally contacts the bottom face of tool insert 10. A ceramic tool seat 60, preferably fabricated of machined alumina-zirconia or zirconia, is pre-sintered at a temperature of about 900° C. Grooves 62 are formed in the bottom face 64 of seat 60 and holes 66 in communication with grooves 62, are then drilled in seat 60. The number of holes 66 (and associated grooves 62) formed in seat 60 depends on the number of sensors to be incorporated into the system which will be further discussed below. Platinum wires 70, having a diameter in the range between about 0.5 to 2 mm, are seated in holes 66 and associated grooves 62.

Figure 4A:
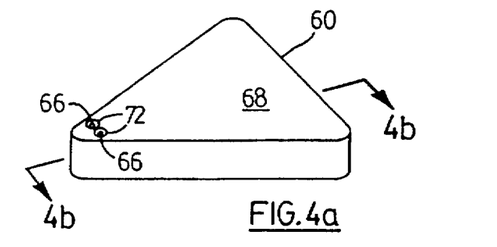
FIG. 4(a) is a perspective view of a ceramic insert seat forming part of another embodiment of the ultrasonic sensor in accordance with the present invention.
Figure 4B:
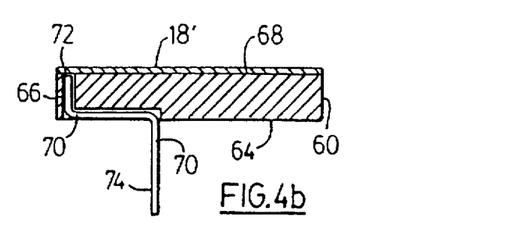
FIG. 4(b) is a sectional view along the line 4(b)—4(b) of FIG. 4(a) with a piezoelectric layer shown in cross section coating the ceramic seat of FIG. 1.
Figures 4C, 5A, 5B, 5C:
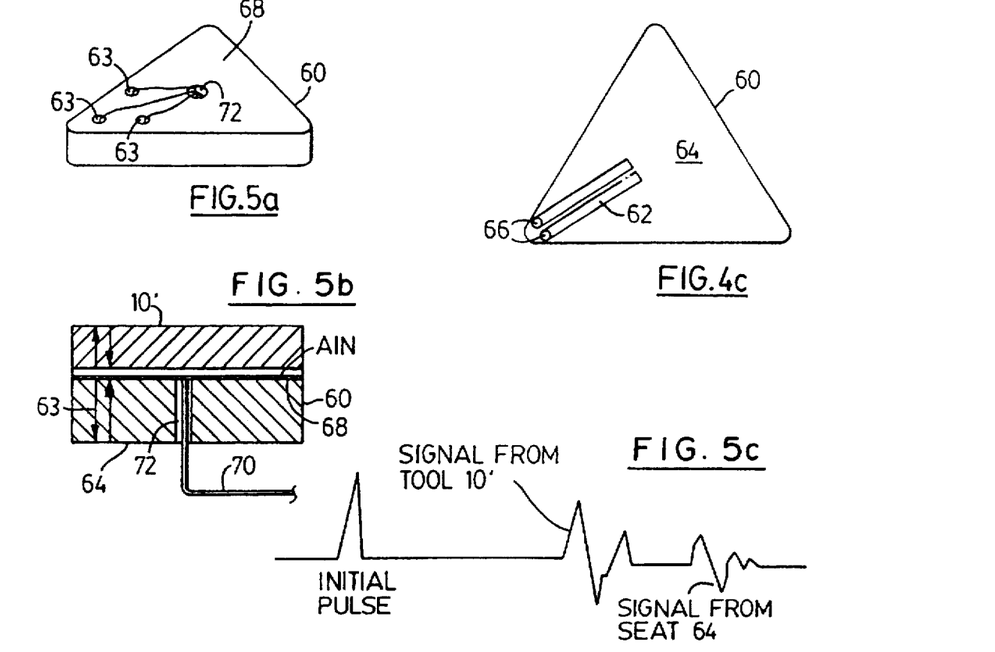
FIG. 4(c) is a bottom view of the seat of FIG. 4(a)
FIG. 5(a) is a perspective view of another embodiment of an insert seat constructed in accordance with the present invention showing an electrode pattern formed on the top surface of the tool insert seat.
FIG. 5(b) is a cross sectional side view of the insert seat of FIG. 5(a) with a tool insert mounted thereon.
FIG. 5(c) shows the time delay between the initial pulse and pulses reflected from the tool insert tip and the bottom face of the insert holder.
Figure 4D:
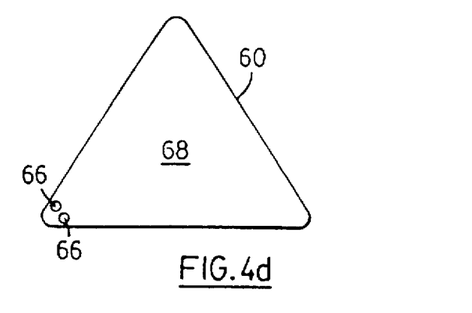
FIG. 4(d) is a top view of the seat of FIG. 4(a)
Figure 4E:
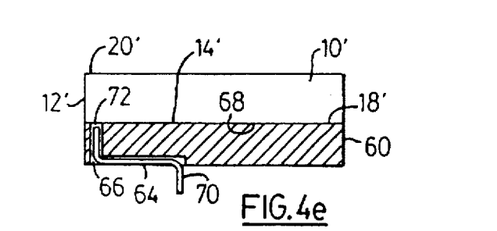
FIG. 4(e) is a sectional view of the insert seat of FIG. 4(a) coated with a piezoelectric layer and assembled with a cutting tool insert.

Referring specifically to FIGS. 4(b) and 4(e), wires 70 are positioned so that the exposed end face 72 of each wire is flush with top surface 68 of seat 60. The seat 60 with wires 70 positioned therein is sintered at a temperature between 1400° to 1500° C. for a period of time between 2 to 8 hours to bond the wires to the ceramic seat. The top surface 68 and face 72 of wires 70 are polished and an AlN coating 18' is deposited thereon. When assembled with cutting tool insert 10', AlN film 18' is sandwiched between wire 70 and the conductive insert as shown in FIG. 4(e). End 74 of wire 70 is connected to a signal generator/analyser (not shown) to be discussed below.

Those skilled in the art will appreciate that any non-conducting ceramic and wire combination may be used provided the ceramic seat is able to withstand the substantial compressive and tensile forces during use of the tool insert such as cutting hard materials. The metal wire must be able to withstand being exposed to the severe deposition conditions required during AlN coating e.g. corrosion resistance due to chlorine or bromine, ammonia and deposition temperatures during formation of the coating (580°–830° C.).

FIGS. 3(a) to 3(d) show one wire 50 contacting the AlN coating 18 and FIGS. 4(a) to 4(e) show two wires 70 spaced apart to contact AlN coating 18' in two positions to form two sensors. Several sensors may be provided depending on the number of wires embedded in the insert seat. Each sensor may be used to monitor and detect different kinds of damage at different locations along the insert cutting edge. The back-reflected signals may be picked up by the same sensor (wire) which emitted the signal or by another sensor located nearby.

Referring to FIG. 5(a), ceramic seat 60 is provided with three electrodes 63 spaced from end face 72 of the sensor wire and electrically connected to the end face by depositing an electrode pattern on the non-conducting surface 68. Top surface 68 is very flat by polishing before deposition of the electrically conducting pattern. In this way multiple sensors may be provided across the surface of the seat. Referring to FIG. 5(b), signal selection is important to discriminate against reflection from bottom face 64 of the seat. This is important since the signal reflected from the insert tip is generally lower intensity than the reflection from bottom face 64.

Figure 6:
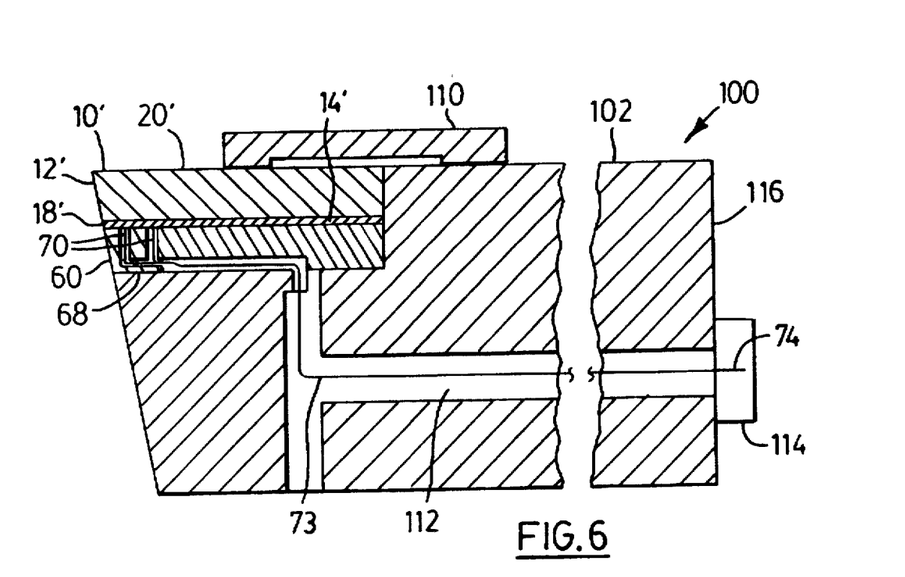
FIG. 6 is a sectional view of an insert holder, cutting tool insert and an insert seat constructed in accordance with the present invention.

A modified standard tool holder 102 with an insert therein assembled with seat 60 and cutting tool insert 10' is shown generally at 100 in FIG. 6. Tool holder 102 includes a cut-out section to receive seat 60 with the AlN film 18' coated on the top surface 68 thereof and cutting tool insert 10' clamped onto the seat by a retaining bracket 110. Seat 60 is provided with two wires 70 contacting the AlN film 18' in two different positions to provide two sensors. Each wire 70 is joined to a coaxial 50 ohm cable 73 (used to excite the AlN film) that passes through a passageway 112 in holder 102 and terminates in a separate BNC electrical connector 114 located at a side edge 116 of the holder.

Figure 7:
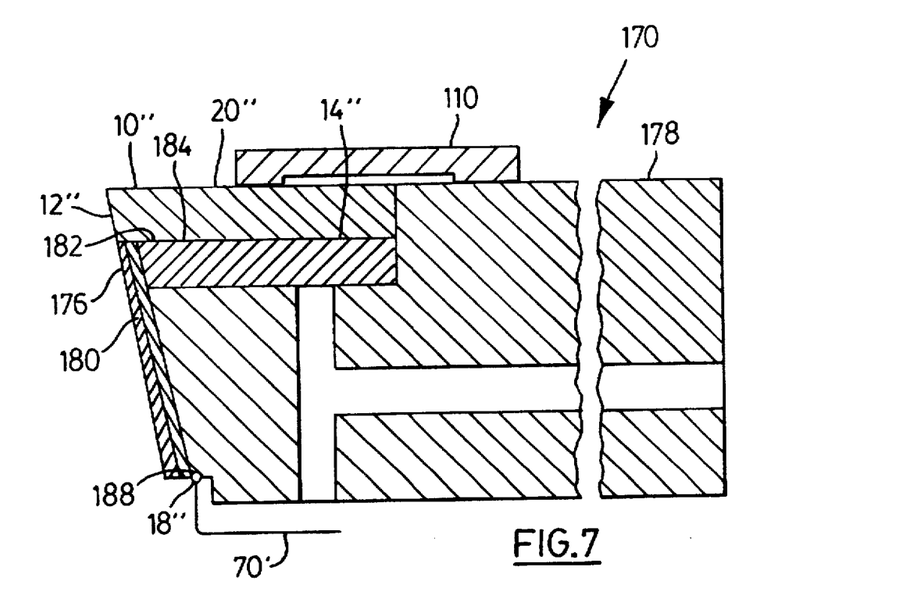
FIG. 7 is a sectional view of another embodiment of an ultrasonic sensor showing a cutting tool insert, insert seat and an insert holder constructed in accordance with the present invention.

An alternative embodiment of the on-line sensor integrated with a cutting tool insert according to the present invention is shown generally at 170 in FIG. 7. A cutting tool insert 10" having a cutting edge 12" is clamped to a tool seat 176 within a tool holder 178'. An elongate ceramic or sapphire rod 180 is seated within cutting tool insert holder 178' and seat 176 with end portion 182 abutting against bottom surface 184 of tool insert 10". The other end portion 188 of rod 180 of is coated or bonded with piezoelectric AlN film 18" which in turn has a wire 70' attached thereto to provide connection to the signal generation and processing circuits (not shown). The elongate rod 180, preferably having a diameter in the range between 0.2 to 2.5 mm is a waveguide and provides a signal delay line which increases mode conversion to permit other wave modes to be transmitted to the signal analyser thereby increasing interference effects and distorting the back-reflected signals.

Figure 8A:
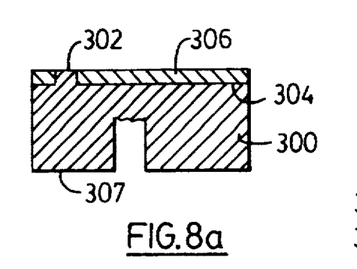
FIG. 8(a) is a sectional side view of an alternative embodiment of a insert tool holder comprising a conductive carbide seat modified to provide a raised conductive electrode adjacent to an insulating ceramic layer.
Figure 8B:
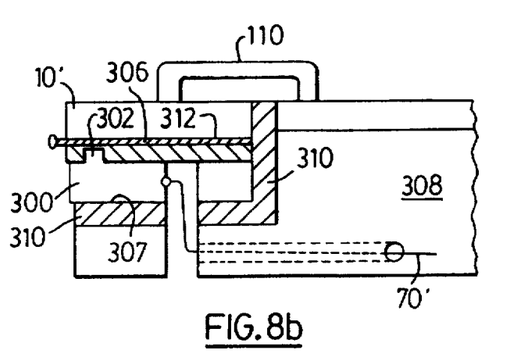
FIG. 8(b) is a sectional side view of the insert seat of FIG. 8(a) mounted in an insert holder.

Referring now to FIG. 8(a), another method of implementing the ultrasonic insert sensor comprises machining a conductive carbide seat 300 to provide a raised electrode 302 above the top surface 304 of the seat and a ceramic layer 306 filling in the machined-out area around raised electrode 302. The top surface 306 of the seat 300 with the ceramic filler is polished flat and the AlN coating 312 is deposited thereon. In this configuration the conductive carbide seat 300 is the positive electrode and therefore it is electrically isolated from the cutting tool insert holder 308, see FIG. 8(b), wherein seat 300 is insulated by ceramic 310 from the insert holder. It will be understood that an acoustic signal will be reflected from backwall 307 of carbide seat 300 as well as from the cutting tip of insert 10'. In order to avoid interference between the signal of interest from the cutting edge of tool insert 10' and the signal reflected from backwall 306, the thickness of carbide seat 300 is chosen to give an appropriate delay between the two sets of signals reaching the signal detector with the carbide insert holder preferably thick enough to ensure the signal from the insert tip reaches the detector first with an appreciable delay from the signal reflected from backwall 306. This embodiment of the device avoids the need for a wire connection directly to the AlN coating.

Those skilled in the art will appreciate that any nonconducting ceramic and wire combination may be used provided the ceramic seat is able to withstand the substantial compressive and tensile forces during use of the insert such as cutting hard materials. The metal wire must be able to withstand being exposed to the severe deposition conditions required during AlN coating e.g. corrosion resistance due to chlorine or bromine, ammonia and deposition temperatures during formation of the coating (580°–830° C.).

ii) AlN Film Growth

The piezoelectric material used to form the sensor is chosen to satisfy the following criteria. First, the piezoelectric coating is able to withstand high temperatures in the range 100°–1000° C.; withstand thermal cycling from room temperature to 1000° C.; and be stable in the presence of coolant liquids. The piezoelectric coating will be strong and hard enough to withstand the high cutting forces encountered during cutting including compressive and tensile forces. Damage to the piezoelectric coating such as chipping or fracturing is accompanied by a change in the ultrasonic signal which results in a false signal.

A second important criteria to be satisfied is that the bond between the piezoelectric film and the substrate (insert— FIG. 3(b); seat—FIG. 4(b)) be thinner than the wavelength of the ultrasonic signal in order to ensure maximum transfer of ultrasonic energy between the piezoelectric coating and the cutting tool insert. This is most readily achieved by depositing the piezoelectric coating directly onto the seat as disclosed for the preferred embodiment illustrated in FIGS. 4(b) to 4(e).

In order to provide strong signal strength in the configuration with the wire embedded in the ceramic seat, good bonding must be provided between the AlN surface and the cutting tool insert. This is best achieved by ensuring the face of the ceramic seat on which the AlN film is deposited is very flat and after deposition of the AlN coating it is then polished flat. In order to transmit the high frequency (50–150 MHz) ultrasound the bonding gap between the AlN surface and the tool insert should be less than quarter-wavelength (less than few micron). Since the surface of the seat or tool holder is not large it may undergo grinding on an optically guided grinding system, e.g. Logitech polishing/ grinding system. The signal strength will not be as strong as in the case when AlN is coated directly on the insert where the bond between the insert and the AlN film is achieved via thin film coating (less than 0.05 microns).

The preferred piezoelectric material is aluminum nitride (AlN) which exhibits the necessary high temperature stability and the mechanical properties to withstand the extreme temperatures and high temperature stresses produced during cutting operations with the tool insert. AlN piezoelectric films are quite hard with a typical hardness of 12 GPa, the highest value known in the piezoelectric group. AlN exhibits very high thermal conductivity (>200 mW/K) and excellent thermal shock stability, and is stable in the presence of standard cutting fluids and thermal gradients. Ultrasonic signals generated in AlN are stable for temperatures <1300° C., which is the temperature range in which most cutting applications occur.

There are several methods for depositing AlN are known to those skilled in the art. Examples of deposition techniques which may be used are chemical vapour deposition (CVD), physical vapour deposition (PVD), PECVD, low pressure chemical vapour deposition (LPCVD), laser ablation, sputtering and molecular beam epitaxy and the like. The deposited AlN film must have <002> crystal orientation in order for the AlN to exhibit piezoelectricity so it can act as the ultrasonic generator and receiver. If the degree of <002> crystal orientation is <95% then the AlN does not exhibit sufficient piezoelectricity to be useful as a sensor.

Suitable AlN films exhibiting the necessary degree of <002> orientation were produced using CVD, LPCVD, and PECVD and were deposited onto several substrates useful as cutting tool inserts, such as carbide and ceramic inserts and alumina-zirconia substrates. Films may be deposited using CVD onto the substrates at temperatures between 730° to 1000° C. from $AlCl_3$ (or $AlBr_3$)—$NH_3/NH_2$—$H_2$ mixtures in an inert carrier gas. Both argon and helium are suitable carrier gases. In one example, the CVD apparatus was made of silica glass and the graphite susceptor holding tools was heated to 600°–750° C. by a 200–400 kHz induction coil. $AlBr_3$ in the liquid phase was reacted with $NH_3$ gas in the reaction chamber using argon as the carrier gas for $AlBr_3$ and $NH_3$. The reaction chamber was maintained at 500° C. and the gas lines in the chamber at 200° C. and the total flow rate of the reactant gases was maintained at 3.4 liters/minute. A $NH_3AlBr_3$ complex was formed which decomposes at >500° C. to form AlN nuclei which after being deposited onto the tool are followed by growth of hexagonal columns. In order to obtain <002> oriented AlN films the temperature and flow rates must be properly maintained as disclosed above.

Using CVD, growth rates greater than 5 nm/second of the AlN films were achieved so that 100 MHz thick films were deposited in less than 30 minutes. CVD is a preferred method for growing the AlN films because interdiffusion between the film and substrate occurs which results in excellent adhesion between the AlN film and the substrate. AlN films with thicknesses between 20–150 microns are preferred. Further details of a process for producing the desirable AlN coatings may be found in Patel, N. D., Boldt, P. H. and Nicholson, P. S. Ceramic Thin and Thick Films, Ceramic Transactions, Vol. 11, American Ceramic Society, (1990), p. 19.

iii) Signal Processing

Figure 9:
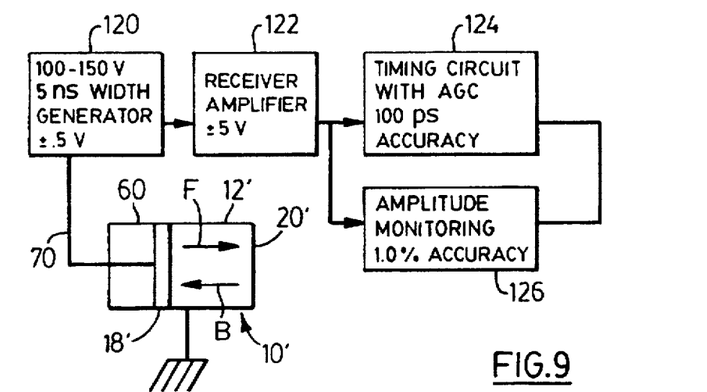
FIG. 9 is a schematic block diagram of the circuit for ultrasonic signal generation and analysis of the back-reflected signals.

FIG. 9 shows a block diagram of an embodiment of a signal generation and detection circuit which forms part of the on-line sensor of the present invention. A high frequency generator 120 is connected to an amplifier 122 used to amplify the voltage signal generated in the piezoelectric layer by the back-reflected ultrasonic signal. The amplified signal is input to a timing circuit 124 and an amplitude monitoring circuit 126.

With reference to FIG. 9, in operation, generator 120 generates a 110 to 150V spike of less than 10 nsec duration which is transmitted along wire 70 to the AlN film 18. When the voltage spike reaches the AlN film 18' it is converted to an ultrasonic signal which propagates through insert 10' in the forward direction indicated by arrow F to top surface 20' in close proximity to cutting edge 12'. The signal is back reflected from top surface 20' as indicated by arrow B and returns to the AlN film. The back reflected signal impinges on AlN film 18' which converts it to a millivolt electrical signal. This signal is amplified by amplifier 122 and the resulting signal is analysed to give both amplitude and the transit time of the back-reflected signal.

The diameters of wires 50 embedded in carbide seat 40 (FIG. 3(b)) and wires 70 located in ceramic seat 60 (FIG. 4(b)) is in the range from about 0.5 to 2.5 mm, (and preferably 0.2 to 2.0 mm) which corresponds to the diameter of the sensor. Sensors in this size range emit high frequency (30 to 150 MHz, corresponding to a 10 to 60 µm film thickness) sound waves with signal strength (signal-to-noise) greater than 40 dB. The rf signals generated by the sensor operating at >30 MHz are unaffected by the low frequency machining noise.

Figure 10:
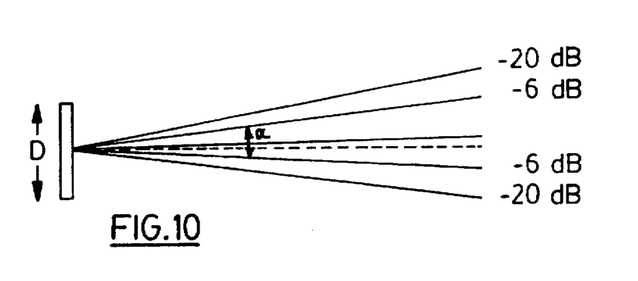
FIG. 10 is a diagrammatic illustration of the relation between source diameter and beam spread angle α.

Referring to FIG. 10, the beam spread angle α at –6 dB is calculated from the relation:

$$\alpha = 2\sin^{-1}(0.5 \lambda/D) \quad (1)$$

where D is the diameter of the source (i.e. the sensor) and λ is the wavelength given by the relation:

$$C = f\lambda \quad (2)$$

where C is the velocity of sound in the insert material and f is the frequency of the sensor used. If the thickness of the insert and the velocity of sound in the insert material is known, then the beam size at the insert cutting face can be calculated using the above relations. For constant thickness inserts of different materials, the beam size will be different at the cutting edge due to the different velocity of sound in each material. If the beam spread angle a is large so that the size of the illuminated edge is very large compared with the chipped or damaged edge portion, then the detection sensitivity decreases. Therefore, the size of the wire and its location with respect to the cutting edge is important to obtaining good detection sensitivity. If the wire diameter is decreased, then from equation (1) above, the beam spread 16 (see FIG. 1) and therefore the size of the area of illumination at the cutting edge 12 increases. As the frequency of the source decreases, the beam spread increases, thereby increasing the illuminated area at the insert edge.

Strategic positions along the cutting edge of the insert can be monitored by appropriate selection of sensor size and positioning of the sensor(s) thereby providing highly directional ultrasonic pulses.

The ultrasonic signal spectra shape is different for different thicknesses of the AlN films and changes with different insert materials being used. All measurements rely on comparing the pre-cutting signal with the signals obtained during or after cutting so that the thickness dependence or material dependence of the signal spectra is not problematic.

Figure 11:
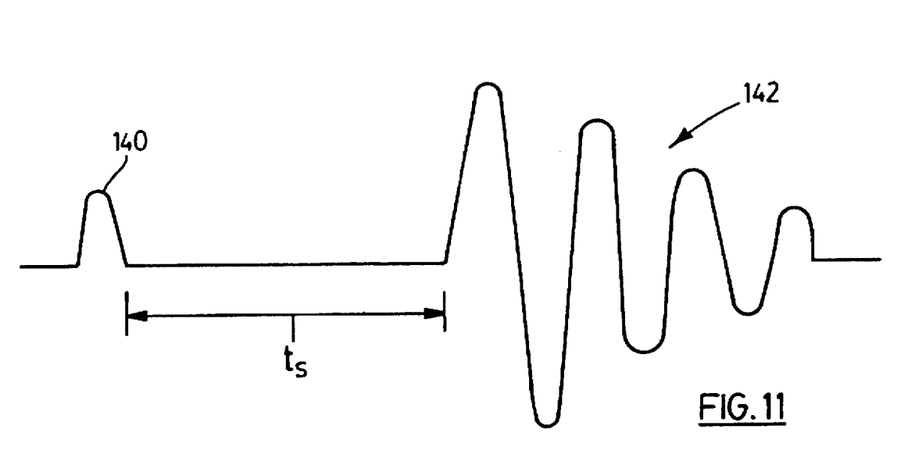
FIG. 11 illustrates a typical signal spectra obtained using the method of the present invention for an undamaged tool insert.

FIG. 11 shows a typical signal versus time obtained for an insert with an undamaged cutting edge. An ultrasonic pulse signal 140 directed to cutting edge 12' is back-reflected and a BAR signal 142 is amplified by amplifier 122 and analysed by circuits 124 and 126 (FIG. 9). The time $t_s$ is the time taken for a round trip of the ultrasonic pulse from the piezoelectric AlN film to cutting edge 12' and back to the AlN film. The shape of signal 142 is a typical signal reflected from an undamaged edge 12'.

Figure 12A:
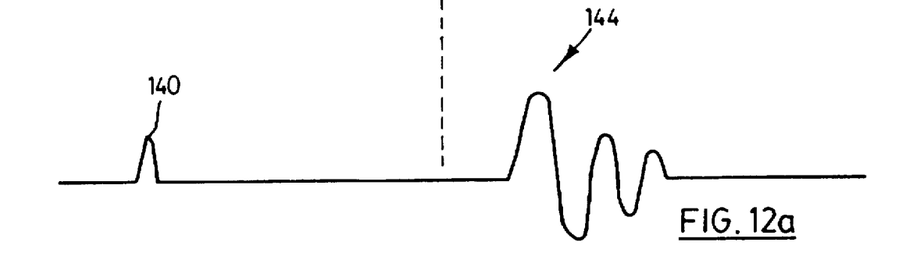
FIG. 12(a) illustrates the effect of temperature rise on the signal spectra for an undamaged tool insert.
Figure 12B:
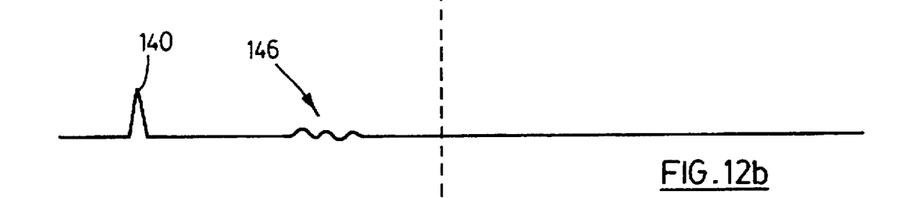
FIG. 12(b) illustrates a signal spectra obtained in a case of complete cutting tool insert failure.
Figure 12C:
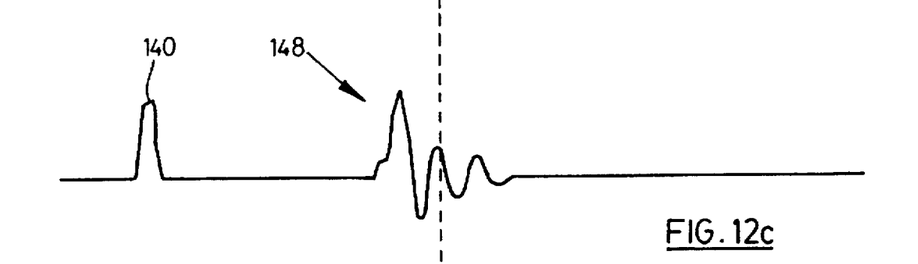
FIG. 12(c) illustrates a signal spectra in a case of insert chipping.
Figure 12D:
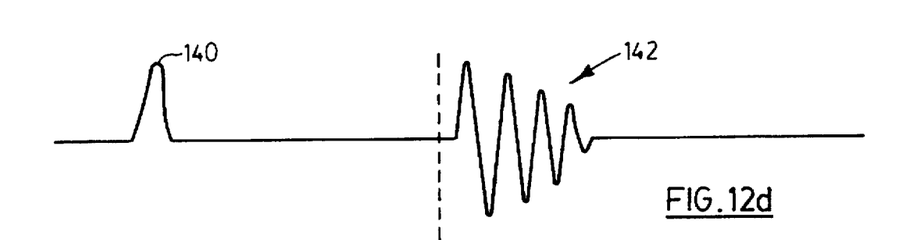
FIG. 12(d) is the same typical signal spectra for an undamaged tool insert shown in FIG. 11 presented for comparison.

In the event that the cutting edge 12' of the insert is damaged, reflected ultrasonic pulse signals significantly different from signal 142 are detected. The reflected signals undergo changes in amplitude, frequency and transit times depending on the type of damage. Referring to FIGS. 12(a) to 12(d), a series of signals characteristic of different types of effects or damage are shown with FIG. 12(d) being characteristic of an undamaged insert edge as shown in FIG. 11. FIG. 12(a) illustrates a signal response at 144 due to a rise in temperature of the cutting edge of the insert. The frequency is decreased slightly compared to signal 142 (FIG. 12(d)) and there is an increase in transit time for the signal to travel from the sensor to the edge and back. FIG. 12(b) shows a signal response 146 characteristic of insert breakage leading to complete failure of the insert. FIG. 12(c) illustrates a signal response 148 typical of chipping of the cutting edge. The transit time is decreased and the signal quality is noticeably degraded with the amplitude also decreased.

In order to obtain 100 picosecond (ps) time resolution within a few milli-seconds (ms) the digitization rate of the signal should be greater than 1 GHz. The time dependent information of the signal is obtained after digitization of the appropriate reflect acoustic signal and the time to obtain the signals will depend upon the averaging speed, digitization rate and the number of sensors used. This approach is expensive and slow if the data acquisition time is important. The best acquisition time obtained using a timing circuit board with 100 ps resolution and a speed in the range 2–20 kHz using a high frequency pulser. Such system can process the data at a speed of 2 ms (500 μs speed for each data point; two amplitudes and two times).

Figure 13:
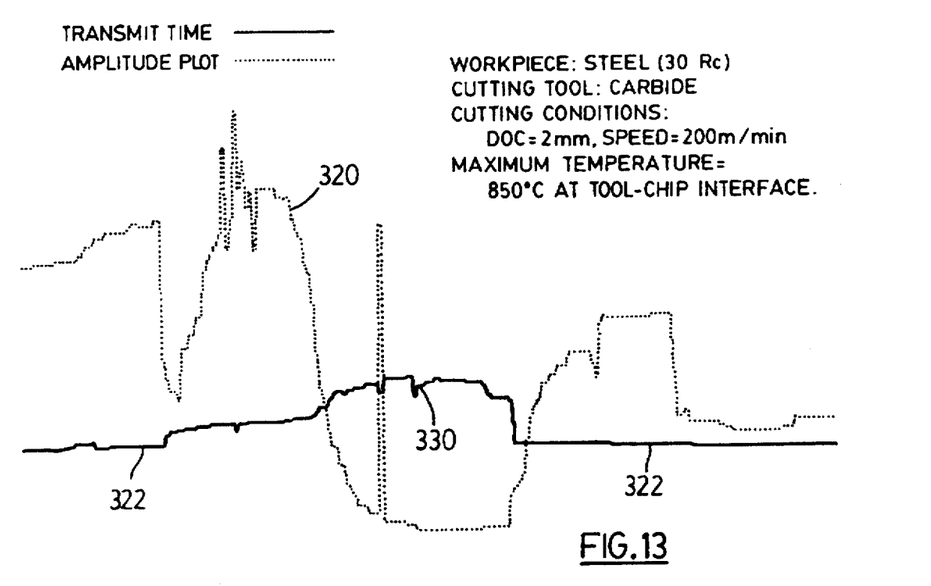
FIG. 13 illustrates the amplitude and time delay signals for cutting a steel workpiece.
Figure 14:
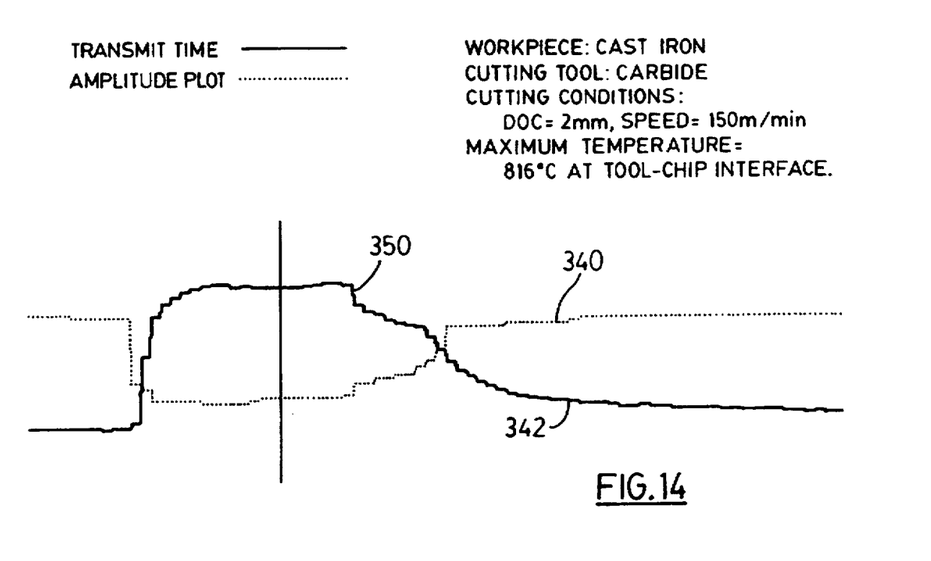
FIG. 14 illustrates the amplitude and time delay signals for cutting a cast iron workpiece.

Typical results obtained with a single channel detection system using an AlN coated carbide insert and steel and cast iron work pieces are shown in FIGS. 13 and 14 respectively. The speed of the cutting is 150 meters/second and the depth of cut was 2 mm. The temperature (within ±5° C.) and wear (accurate to within a few microns) information was obtained. For reliable temperature measurements the calibration of the insert with a standard heat source was carried out. The signal time was monitored as a function of the insert tip temperature using a very fine heat source with the thermocouple placed at the measurement point. The temperature information was obtained from the calibration curve.

As previously discussed, a good intimate bond between the AlN coating and the tool insert is important for optimum transmission of the acoustic energy between the tool insert and the detector. The inventors have observed that the same is true for the cutting tool insert and workpiece interface. In case of seizure the best bond between the insert face and the workpiece is obtained and maximum energy will be transferred from the insert tip into the workpiece. This suggests that the insert-tip interface may also be studied using the device disclosed herein by monitoring the amplitude of the acoustic signal. The amplitude will decrease with the insert-chip interface and also with an increase in the contact area size between the insert and tip.

The signal obtained while cutting a steel workpiece shown in FIG. 13 shows that the amplitude signal 320 decreases initially and then increases. The transit time signal 322 increases with the temperature. This result is interpreted to mean that initially the contact point (seizure) is at the insert tip and that the contact point is lost as the cutting progresses. The seizure starts occurring slightly away from the tip at a temperature >300° C. and temperature rises very fast to a constant value of about 850° C. (i.e. time sign increases) and the amplitude decreases very rapidly and steady value is reached at constant temperature. Occasionally a very rapid decrease of the transit time signal is seen of a very small value as shown at 330, suggesting a very small chip or particle of micron dimensions breaks off the tool. If the chipping is large then the time signal will drop very rapidly and will not recover to its original value (not seen in FIG. 13). By comparing the starting value and the final value of the transit time (when the insert is at same temperature) the value of the wear can be calculated which in the data of FIG. 13 it is about 1.8 micron.

The behaviour of cast iron during cutting is completely different as seen in FIG. 14. While steel exhibits a two stage cutting process, iron exhibits a single stage cutting process. The contact area of the chip is near the insert tip. As the cutting progresses, the seizure occurs near the tip and amplitude signal 340 decreases and time signal 342 decreases increases indicating a temperature increase. Within a few seconds a steady state is reached in which the amplitude and time signals remain relatively constant. About 8 seconds from the start of the cut about 2 micron chip comes from the insert which is accompanied by a very steep decrease in time signal shown at 350 in FIG. 14. After the cutting operation was completed the insert was examined to confirm chipping did occur.

While the on-line ultrasonic sensor constructed in accordance with the present invention has been described and illustrated with respect to the preferred and alternative embodiments, it will be appreciated by those skilled in the art that numerous other embodiments of the sensor may be made without departing from the scope of the invention disclosed herein.

Therefore what is claimed is:

1. A method for on-line monitoring a tool insert having an edge portion which contacts a workpiece during use, comprising:
   a) producing ultrasonic signal pulses in a coating of piezoelectric material contacting a tool insert and directing the ultrasonic signal pulses through the tool insert toward said edge portion of the tool insert;
   b) detecting ultrasonic signal pulses reflected from said edge portion of the tool insert back into the piezoelectric coating; and
   c) comparing said ultrasonic signal pulses reflected from said edge portion of the tool insert to reference ultrasonic signal pulses reflected from said edge portion before the tool insert is initially contacted to said workpiece.

2. The method according to claim 1 wherein the step of detecting the ultrasonic signal pulses comprises measuring a transit time of each one of the ultrasonic signal pulses from a source electrode to said edge portion and back to said source electrode.

3. The method according to claim 1 wherein the step of detecting the ultrasonic signal pulses comprises measuring an amplitude of each one of the ultrasonic signal pulses.

4. The method according to claim 1 wherein said piezoelectric coating is a film of aluminum nitride (AlN) having substantially <002> crystal orientation.

5. The method according to claim 4 wherein said AlN film has a thickness in the range from about 20 μm to about 150 μm.

6. The method according to claim 2 wherein said reflected ultrasonic signal pulses are analyzed to determine the transit time of the ultrasonic signal pulses in use and comparing said transit time to the transit time for the reference ultrasonic signal pulses.

7. The method according to claim 3 wherein said reflected ultrasonic signal pulses are analyzed to determine its amplitude and comparing said amplitude to the amplitude for the reference ultrasonic signal pulses.

8. The method according to claim 4 wherein the AlN coating is grown on a surface of an insert seat to which the tool insert is clamped so that in use the AlN coating is sandwiched between the tool insert and the insert seat.

9. The method according to claim 4 wherein the AlN coating is grown on a surface of the tool insert which is adjacent to a surface of an insert seat on which the tool insert is clamped so that in use the AlN coating is sandwiched between the tool insert and the insert seat.

10. The method according to claim 5 wherein the ultrasonic signal pulses have a frequency in the range from about 30 MHZ to about 150 MHZ.

11. An on-line ultrasonic sensor for monitoring a tool insert, the tool insert having an edge portion for contacting a workpiece and being mountable in an insert holder, comprising:
   a) a piezoelectric coating in contact with a portion of said tool insert spaced from said edge portion;
   b) means for generating ultrasonic signal pulses in the piezoelectric coating, the ultrasonic signal pulses being directed through the tool insert substantially toward said edge portion of the tool insert which contacts said workpiece in use; and c) means for detecting and analyzing ultrasonic signal pulses responsively reflected from said edge portion of the tool insert back through the tool insert into the piezoelectric coating.

12. The on-line sensor according to claim 11 wherein the piezoelectric coating is a film of aluminum nitride (AlN) having substantially <002> crystal orientation.

13. The on-line sensor according to claim 12 wherein said AlN film has a thickness in the range from about 20 μm to about 150 μm.

14. The on-line sensor according to claim 12 wherein said insert holder includes a seat, the tool insert being clamped onto the seat in the insert holder, and wherein the AlN coating is grown on a surface of the seat to which the tool insert is clamped in use so the AlN coating is sandwiched between the tool insert and the seat and contacts both.

15. The on-line sensor according to claim 14 wherein said means for generating said ultrasonic signal pulses includes a voltage generator electrically coupled to said AlN coating.

16. The on-line sensor according to claim 15 wherein in use said signal analyzing means includes means for measuring a transit time of the ultrasonic signal pulses from a source electrode to the edge portion and back to the source, and comparing said transit time to a transit time for reference ultrasonic signal pulses reflected from said edge portion before the tool insert is contacted to the workpiece.

17. The on-line sensor according to claim 15 wherein said signal analyzing means includes means for measuring an amplitude of the reflected ultrasonic signal pulses and comparing said amplitude to an amplitude for a reference ultrasonic signal pulse reflected from said edge portion before the tool insert is contacted to the workpiece.

18. The on-line sensor according to claim 12 wherein said insert holder includes a seat, the tool insert being clamped onto the seat in the insert holder, and wherein the AlN coating is grown on a surface of the tool insert which is adjacent to the seat so that the AlN coating is sandwiched between the tool insert and the seat and contacts both.

19. The on-line sensor according to claim 18 wherein said means for generating said ultrasonic signal pulses includes a voltage generator electrically coupled to said AlN coating.

20. The on-line sensor according to claim 19 wherein said signal analyzing means includes means for measuring a transit time of the ultrasonic signal pulse from a source electrode to the edge portion and back to the source and comparing said transit time to a transit time of a reference ultrasonic signal pulse reflected from said edge portion before the tool insert is contacted to the workpiece.

21. The on-line sensor according to claim 19 wherein said signal analyzing means includes means for measuring an amplitude of the reflected ultrasonic pulses and comparing said amplitude to an amplitude of at least one reference ultrasonic signal pulse reflected from said edge portion before the tool insert is contacted to the workpiece.

* * * * *